US012692242B2

(12) United States Patent
Tao et al.

(10) Patent No.: US 12,692,242 B2
(45) Date of Patent: Jul. 28, 2026

(54) METHOD FOR PREPARING FLURALANER

(71) Applicant: Hangzhou Normal University, Hangzhou (CN)

(72) Inventors: Lianzhi Tao, Hangzhou (CN); Weiming Xu, Hangzhou (CN); Yixian Chen, Hangzhou (CN); Zhiwei Fan, Hangzhou (CN); Hui Liu, Hangzhou (CN); Pengfei Zhang, Hangzhou (CN); Dongxiang Feng, Hangzhou (CN)

(73) Assignee: Hangzhou Normal University, Hangzhou (CN)

( * ) Notice: Subject to any disclaimer, the term of this patent is extended or adjusted under 35 U.S.C. 154(b) by 359 days.

(21) Appl. No.: 18/611,683

(22) Filed: Mar. 20, 2024

(65) Prior Publication Data

US 2025/0214950 A1 Jul. 3, 2025

(30) Foreign Application Priority Data

Jan. 3, 2024 (CN) ......................... 202410010104.4

(51) Int. Cl.
*C07D 261/04* (2006.01)

(52) U.S. Cl.
CPC .................................. *C07D 261/04* (2013.01)

(58) Field of Classification Search
CPC .................................................. C07D 261/04
See application file for complete search history.

(56) References Cited

FOREIGN PATENT DOCUMENTS

WO WO-2020088949 A1 * 5/2020 ........... C07D 261/04

* cited by examiner

*Primary Examiner* — Shawquia Jackson
(74) *Attorney, Agent, or Firm* — Morgan, Lewis & Bockius LLP

(57) ABSTRACT

Provided is a method for preparing fluralaner. The method includes: mixing 4-(5-(3,5-dichlorophenyl)-5-(trifluoromethyl)-4,5-dihydro-isoxazol-3-yl)-2-methyl-benzoic acid, a catalyst, an alcohol and an organic solvent to obtain a mixture, and subjecting the mixture to esterification to obtain an esterification solution containing 4-(5-(3,5-dichlorophenyl)-5-(trifluoromethyl)-4,5-dihydro-isoxazol-3-yl)-2-methyl-benzoate; and mixing the esterification solution with 2-amino-N-(2,2,2-trifluoroethyl)acetamide to obtain a mixed solution and subjecting the mixed solution to ester decomposition-amidation to obtain the fluralaner.

14 Claims, 3 Drawing Sheets

Signal:VWD1A,Wavelength=256 nm

| Retention time [min] | Type | Peak width [min] | Peak area | Height | Peak area % | Name |
|---|---|---|---|---|---|---|
| 8.591 | MM m | 0.07 | 0.13 | 0.03 | 0.00 | |
| 8.823 | MM m | 0.05 | 0.15 | 0.04 | 0.00 | |
| 9.436 | MM m | 0.08 | 0.52 | 0.10 | 0.01 | |
| 9.674 | MM m | 0.08 | 1.03 | 0.19 | 0.01 | |
| 15.295 | MM m | 0.10 | 1.56 | 0.23 | 0.01 | |
| 15.629 | MM m | 0.09 | 0.68 | 0.11 | 0.01 | |
| 17.341 | MM m | 0.13 | 5.67 | 0.64 | 0.05 | |
| 17.708 | MM m | 0.12 | 0.71 | 0.09 | 0.01 | |
| 18.133 | MM m | 0.10 | 0.67 | 0.10 | 0.01 | |
| 19.224 | BB | 0.54 | 10406.66 | 1294.36 | 99.75 | |
| 20.969 | MM m | 0.23 | 12.75 | 0.74 | 0.12 | |
| 22.563 | MM m | 0.14 | 1.91 | 0.19 | 0.02 | |
| | | Total | 10432.45 | | | |

METHOD FOR PREPARING FLURALANER

CROSS REFERENCE TO RELATED APPLICATION

This application claims the benefit and priority of Chinese Patent Application No. 2024100101044, filed with the China National Intellectual Property Administration on Jan. 3, 2024, the disclosure of which is incorporated by reference herein in its entirety as part of the present application.

TECHNICAL FIELD

The present disclosure belongs to the technical field of chemical synthesis, and specifically relates to a method for preparing fluralaner.

BACKGROUND

Fluralaner, as an isoxazoline broad-spectrum insecticide as well as acaricide used for the treatment of animal parasites, has been currently registered and marketed as a veterinary drug with a trade name Bravectotm and a structural formula shown below:

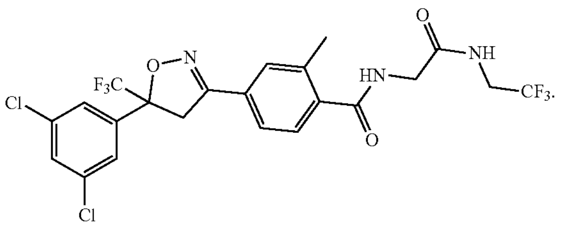 [SMILES: Cc1cc(C2=NOC(c3cc(Cl)cc(Cl)c3)(C(F)(F)F)C2)ccc1C(=O)NCC(=O)NCC(F)(F)F]

Similar to the targets of insecticides such as cyclopentadienes, phenylpyrazoles, and macrolides, the fluralaner mainly works by interfering with γ-aminobutyric acid (GABA)-gated chloride ion channels, and has a desirable insecticidal effect on pests of Ixodida, Siphonaptera, Anoplura, Hemiptera, and Diptera.

At present, it is reported that the fluralaner is mainly prepared by a reaction of 4-(5-(3,5-dichlorophenyl)-5-(trifluoromethyl)-4,5-dihydro-isoxazol-3-yl)-2-methyl-benzoic acid with 2-amino-N-(2,2,2-trifluoroethyl)acetamide. However, this process requires converting 4-(5-(3,5-dichlorophenyl)-5-(trifluoromethyl)-4,5-dihydro-isoxazol-3-yl)-2-methyl-benzoic acid into 4-(5-(3,5-dichlorophenyl)-5-(trifluoromethyl)-4,5-dihydro-isoxazol-3-yl)-2-methyl-benzoyl chloride, during which at least equivalent amount of acylation reagent such as thionyl chloride or phosphorus trichloride is required. The acylation reagent could produce a large amount of waste acid during the reaction, and neutralizing the waste acid will produce a large amount of salt, resulting in deficiencies such as large pollution and serious three waster (wastewater, exhaust gas, and solid waste) problems.

SUMMARY

In view of this, an object of the present disclosure is to provide a method for preparing fluralaner. The method according to the present disclosure has simple operations without need of an acylation reagent, thus avoiding serious pollution existing in traditional preparation methods.

To achieve the above object, the present disclosure provides the following technical solutions.

The present disclosure provides a method for preparing fluralaner, including the following steps: mixing 4-(5-(3,5-dichlorophenyl)-5-(trifluoromethyl)-4,5-dihydro-isoxazol-3-yl)-2-methyl-benzoic acid, a catalyst, an alcohol and an organic solvent to obtain a mixture, and subjecting the mixture to esterification to obtain an esterification solution containing 4-(5-(3,5-dichlorophenyl)-5-(trifluoromethyl)-4,5-dihydro-isoxazol-3-yl)-2-methyl-benzoate; and mixing the esterification solution and 2-amino-N-(2,2,2-trifluoroethyl)acetamide to obtain a mixed solution, and subjecting the mixed solution to ester decomposition-amidation to obtain the fluralaner.

In some embodiments, the catalyst is one or more selected from the group consisting of p-toluenesulfonic acid, sulfuric acid, phosphoric acid, sulfonic acid resin, phosphotungstic acid, silicotungstic acid, and an aluminosilicate molecular sieve.

In some embodiments, a weight ratio of the catalyst to the 4-(5-(3,5-dichlorophenyl)-5-(trifluoromethyl)-4,5-dihydro-isoxazol-3-yl)-2-methyl-benzoic acid is in a range of (0.001-0.2):1.

In some embodiments, the alcohol is one or more selected from the group consisting of methanol, ethanol, isopropanol, and n-propanol.

In some embodiments, a molar ratio of the alcohol to the 4-(5-(3,5-dichlorophenyl)-5-(trifluoromethyl)-4,5-dihydro-isoxazol-3-yl)-2-methyl-benzoic acid is in a range of (1-10):1.

In some embodiments, the organic solvent is one or more selected from the group consisting of toluene, xylene, ethylbenzene, and cyclohexane.

In some embodiments, a weight ratio of the organic solvent to the 4-(5-(3,5-dichlorophenyl)-5-(trifluoromethyl)-4,5-dihydro-isoxazol-3-yl)-2-methyl-benzoic acid is in a range of (2-8):1.

In some embodiments, the esterification is conducted at a temperature of 70° C. to 130° C. for 2 h to 10 h.

In some embodiments, a molar ratio of the 2-amino-N-(2,2,2-trifluoroethyl)acetamide to the 4-(5-(3,5-dichlorophenyl)-5-(trifluoromethyl)-4,5-dihydro-isoxazol-3-yl)-2-methyl-benzoic acid is in a range of (1-3):1.

In some embodiments, the ester decomposition-amidation is conducted at a temperature of 90° C. to 150° C. for 3 h to 12 h.

Compared with the prior art, some embodiments of the present disclosure have the following beneficial effects.

The present disclosure provides a method for preparing fluralaner, including: mixing 4-(5-(3,5-dichlorophenyl)-5-(trifluoromethyl)-4,5-dihydro-isoxazol-3-yl)-2-methyl-benzoic acid, a catalyst, an alcohol and an organic solvent to obtain a mixture, and subjecting the mixture to esterification to obtain an esterification solution containing 4-(5-(3,5-dichlorophenyl)-5-(trifluoromethyl)-4,5-dihydroisoxazol-3-yl)-2-methylbenzoate; and mixing the esterification solution and 2-amino-N-(2,2,2-trifluoroethyl)acetamide to obtain a mixed solution and subjecting the mixed solution to ester decomposition-amidation to obtain the fluralaner. In the present disclosure, the 4-(5-(3,5-dichlorophenyl)-5-(trifluoromethyl)-4,5-dihydro-isoxazol-3-yl)-2-methyl-benzoic acid as a raw material is subjected to esterification, and a resulting esterification solution is then directly subjected to ester decomposition-amidation with the 2-amino-N-(2,2,2-trifluoroethyl)acetamide without a post-treatment, such that the fluralaner is successfully prepared by using a one-pot method. The method according to the present disclosure has simple operations without need of an acylation reagent, thus avoiding serious pollution existing in traditional preparation methods. Moreover, the method has a high yield, which is not less than 98% in the examples.

BRIEF DESCRIPTION OF THE DRAWINGS

To describe the technical solutions in embodiments of the present disclosure or in the prior art more clearly, the accompanying drawings used in the embodiments are briefly described below. Apparently, the accompanying drawings in the following description show merely some embodiments of the present disclosure, and those of ordinary skill in the art may still derive other accompanying drawings from these accompanying drawings without creative efforts.

DETAILED DESCRIPTION OF THE EMBODIMENTS

Figure 1:
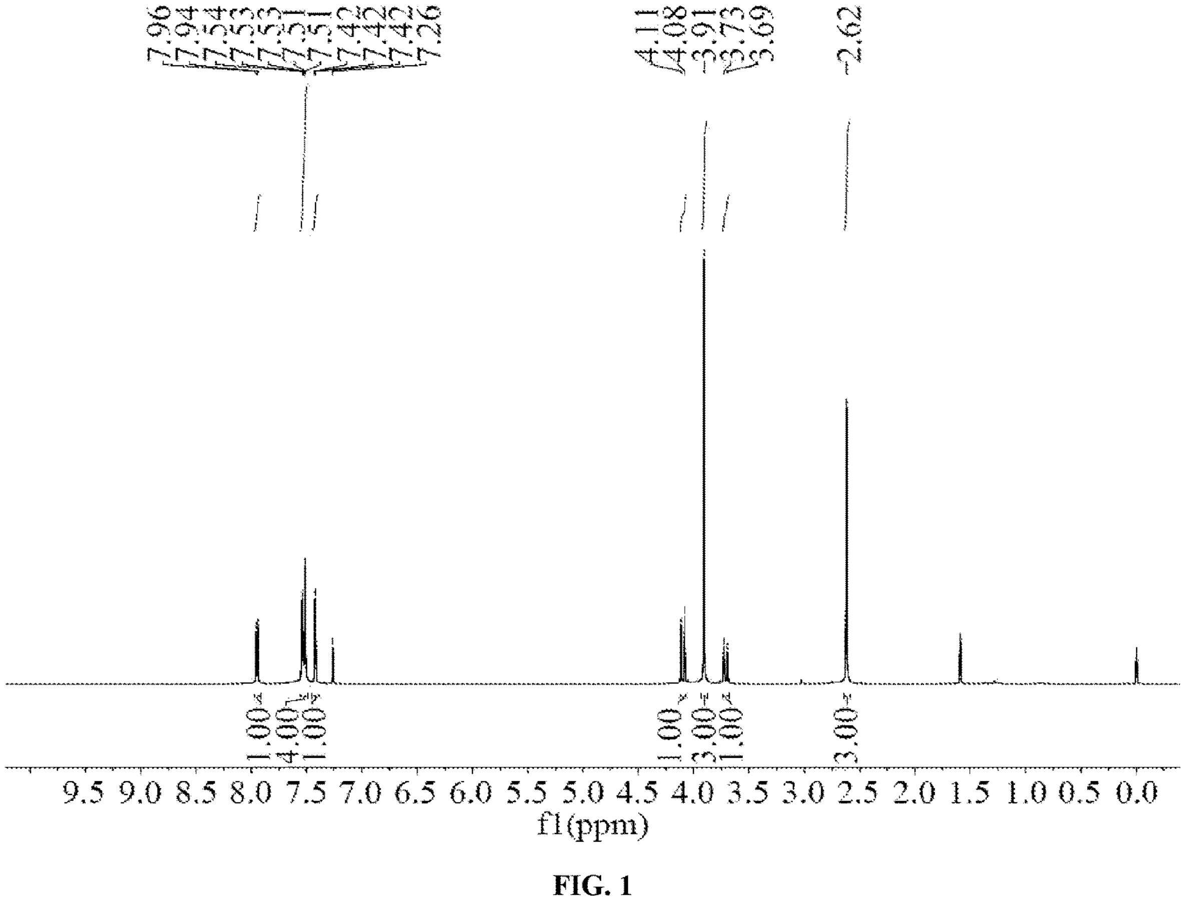
FIG. 1 shows a hydrogen nuclear magnetic resonance (HNMR) spectrum of the 4-(5-(3,5-dichlorophenyl)-5-(trifluoromethyl)-4,5-dihydro-isoxazol-3-yl)-2-methyl-benzoate prepared in Example 1.

The present disclosure provides a method for preparing fluralaner, including the following steps: mixing 4-(5-(3,5-dichlorophenyl)-5-(trifluoromethyl)-4,5-dihydro-isoxazol-3-yl)-2-methyl-benzoic acid, a catalyst, an alcohol and an organic solvent to obtain a mixture, and subjecting the mixture to esterification to obtain an esterification solution containing 4-(5-(3,5-dichlorophenyl)-5-(trifluoromethyl)-4,5-dihydro-isoxazol-3-yl)-2-methyl-benzoate; and mixing the esterification solution and 2-amino-N-(2,2,2-trifluoroethyl)acetamide to obtain a mixed solutions, and subjecting the mixed solutions to ester decomposition-amidation to obtain the fluralaner.

In the present disclosure, unless otherwise specified, all materials and equipment used herein are commercially available in the art.

In some embodiments, 4-(5-(3,5-dichlorophenyl)-5-(trifluoromethyl)-4,5-dihydro-isoxazol-3-yl)-2-methyl-benzoic acid, a catalyst, an alcohol and an organic solvent are mixed and then subjected to esterification to obtain an esterification solution containing 4-(5-(3,5-dichlorophenyl)-5-(trifluoromethyl)-4,5-dihydro-isoxazol-3-yl)-2-methyl-benzoate.

In some embodiments, the catalyst is one or more selected from the group consisting of p-toluenesulfonic acid, sulfuric acid, phosphoric acid, sulfonic acid resin, phosphotungstic acid, silicotungstic acid, and an aluminosilicate molecular sieve. The catalyst does not form a stable salt of the raw material carboxylic acid to hinder the occurrence of esterification.

In some embodiments, a weight ratio of the catalyst to the 4-(5-(3,5-dichlorophenyl)-5-(trifluoromethyl)-4,5-dihydro-isoxazol-3-yl)-2-methyl-benzoic acid is in a range of preferably (0.001-0.2):1, preferably (0.01-0.1):1.

In some embodiments, the alcohol is one or more selected from the group consisting of methanol, ethanol, isopropanol, and n-propanol. In some embodiments, the alcohol is a low-boiling alcohol, which could be easily distilled out directly after the ester decomposition-amidation, thereby promoting the equilibrium to shift toward product formation.

In some embodiments, a molar ratio of the alcohol to the 4-(5-(3,5-dichlorophenyl)-5-(trifluoromethyl)-4,5-dihydro-isoxazol-3-yl)-2-methyl-benzoic acid is in a range of (1-10):1, preferably (2-8):1.

In some embodiments, the organic solvent is one or more selected from the group consisting of toluene, xylene, ethylbenzene, and cyclohexane.

In some embodiments, a weight ratio of the organic solvent to the 4-(5-(3,5-dichlorophenyl)-5-(trifluoromethyl)-4,5-dihydro-isoxazol-3-yl)-2-methyl-benzoic acid is in a range of (2-8):1, preferably (3-6):1.

In some embodiments, the esterification is conducted at a temperature of 70° C. to 130° C., preferably 80° C. to 110° C., and the esterification is conducted for 2 h to 10 h, preferably 3 h to 5 h. The esterification is conducted according to a reaction formula shown in formula I. The 4-(5-(3,5-dichlorophenyl)-5-(trifluoromethyl)-4,5-dihydro-isoxazol-3-yl)-2-methyl-benzoic acid (I) and the alcohol are subjected to the esterification to generate 4-(5-(3,5-dichlorophenyl)-5-(trifluoromethyl)-4,5-dihydro-isoxazol-3-yl)-2-methyl-benzoate (II).

Formula I

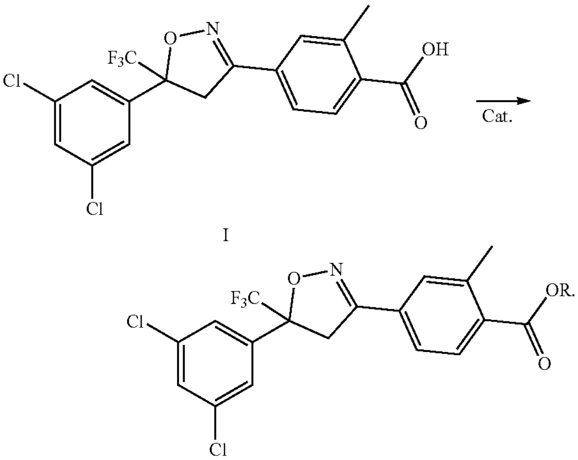

I

II

In some embodiments, the 4-(5-(3,5-dichlorophenyl)-5-(trifluoromethyl)-4,5-dihydro-isoxazol-3-yl)-2-methyl-benzoic acid, the catalyst, the alcohol, and the organic solvent are mixed in a reaction vessel equipped with a thermometer, a stirrer, and a water separator. The esterification is stopped until no more water is produced in the system.

In some embodiments, cooling is conducted after the esterification, and the cooling is conducted to reach a temperature of 50° C.

After an esterification solution containing 4-(5-(3,5-dichlorophenyl)-5-(trifluoromethyl)-4,5-dihydro-isoxazol-3-yl)-2-methyl-benzoate is obtained, the esterification solution and 2-amino-N-(2,2,2-trifluoroethyl)acetamide are mixed and then subjected to ester decomposition-amidation to obtain the fluralaner.

In some embodiments, a molar ratio of the 2-amino-N-(2,2,2-trifluoroethyl)acetamide to the 4-(5-(3,5-dichlorophenyl)-5-(trifluoromethyl)-4,5-dihydro-isoxazol-3-yl)-2-methyl-benzoic acid is in a range of (1-3):1, preferably 2:1.

In some embodiments, the ester decomposition-amidation is conducted at a temperature of 90° C. to 150° C., preferably 120° C. to 130° C., and the ester decomposition-amidation is conducted for 3 h to 12 h, preferably 5 h to 7 h. The ester decomposition-amidation is conducted according to a reaction formula shown in formula II. The 4-(5-(3,5-dichlorophenyl)-5-(trifluoromethyl)-4,5-dihydro-isoxazol-3-yl)-2-methyl-benzoate (II) and the 2-amino-N-(2,2,2-trifluoroethyl)acetamide are subjected to the ester decomposition-amidation to generate the fluralaner (III).

Formula II

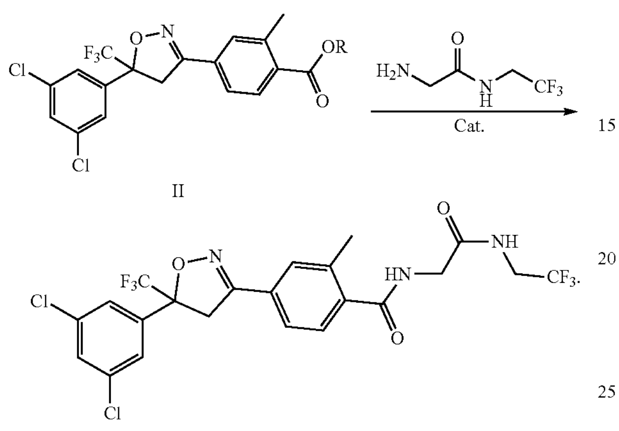

II

III

In some embodiments, the ester decomposition-amidation is stopped until no more alcohol is produced in the system.

In some embodiments, a post-treatment is conducted after the ester decomposition-amidation, and the post-treatment is conducted by cooling, washing, solvent removal, and drying in sequence to obtain the fluralaner. In some embodiments, under the condition that the catalyst is a solid, solid-liquid separation is conducted after the cooling, and the solid-liquid separation is conducted by filtration, and a liquid obtained after the filtration contains the fluralaner.

In some embodiments, under the condition that the molar ratio of the 2-amino-N-(2,2,2-trifluoroethyl)acetamide to the 4-(5-(3,5-dichlorophenyl)-5-(trifluoromethyl)-4,5-dihydro-isoxazol-3-yl)-2-methyl-benzoic acid is 1:1, the washing is conducted by water washing. In some embodiments, under the condition that the molar ratio of the 2-amino-N-(2,2,2-trifluoroethyl)acetamide to the 4-(5-(3,5-dichlorophenyl)-5-(trifluoromethyl)-4,5-dihydro-isoxazol-3-yl)-2-methyl-benzoic acid is greater than 1:1, the washing is conducted by acid washing and water washing in sequence; a reagent used in the acid washing is a hydrochloric acid solution, and the acid washing is to salify excess organic amine and dissolve a resulting salt in an aqueous phase.

In some embodiments, the solvent removal is conducted by atmospheric distillation.

In some embodiments, the drying is conducted at a temperature of 30° C. to 70° C., and the drying is conducted for 2 h to 6 h.

In order to further illustrate the present disclosure, the method for preparing fluralaner according to the present disclosure is described in detail below in conjunction with accompanying drawings and examples, but these examples should not be understood as limiting the scope of the present disclosure.

EXAMPLE 1

418 g of 4-(5-(3,5-dichlorophenyl)-5-(trifluoromethyl)-4,5-dihydro-isoxazol-3-yl)-2-methyl-benzoic acid, 2.0 g of p-toluenesulfonic acid, 2.0 g of phosphotungstic acid, 50 g of methanol, and 1,200 g of toluene were added into a reaction vessel equipped with a thermometer, a stirrer, and a water separator. A resulting mixture was subjected to reaction at a temperature of 90° C. to 100° C. for 5 h while fractionating water produced during the reaction, and then cooled to 50° C. to obtain a cooled mixture. 163.5 g of 2-amino-N-(2,2,2-trifluoroethyl)acetamide was added into the cooled mixture and then subjected to reaction at a temperature of 120° C. to 125° C. for 3 h while fractionating methanol produced during the reaction. After the reaction is completed, filtration was conducted, and a resulting organic layer was washed by using 500 g of hydrochloric acid with a pH of 1 and 300 g of water in sequence. A resulting product was subjected to atmospheric distillation to recover solvent, and a remaining product was dried to obtain 551.1 g of a white solid fluralaner product with a purity of 99.75% and a yield of 99.1%.

FIG. 1 shows an HNMR spectrum of the 4-(5-(3,5-dichlorophenyl)-5-(trifluoromethyl)-4,5-dihydro-isoxazol-3-yl)-2-methyl-benzoate prepared in Example 1. $^1H$ NMR (500 MHz, $CDCl_3$): δ7.95 (d, J=8.7 Hz, 1H), 7.55-7.49 (m, 4H), 7.42 (t, J=1.8 Hz, 1H), 4.10 (d, J=17.2 Hz, 1H), 3.91 (s, 3H), 3.71 (d, J=17.2 Hz, 1H), 2.62 (s, 3H).

Figure 2:
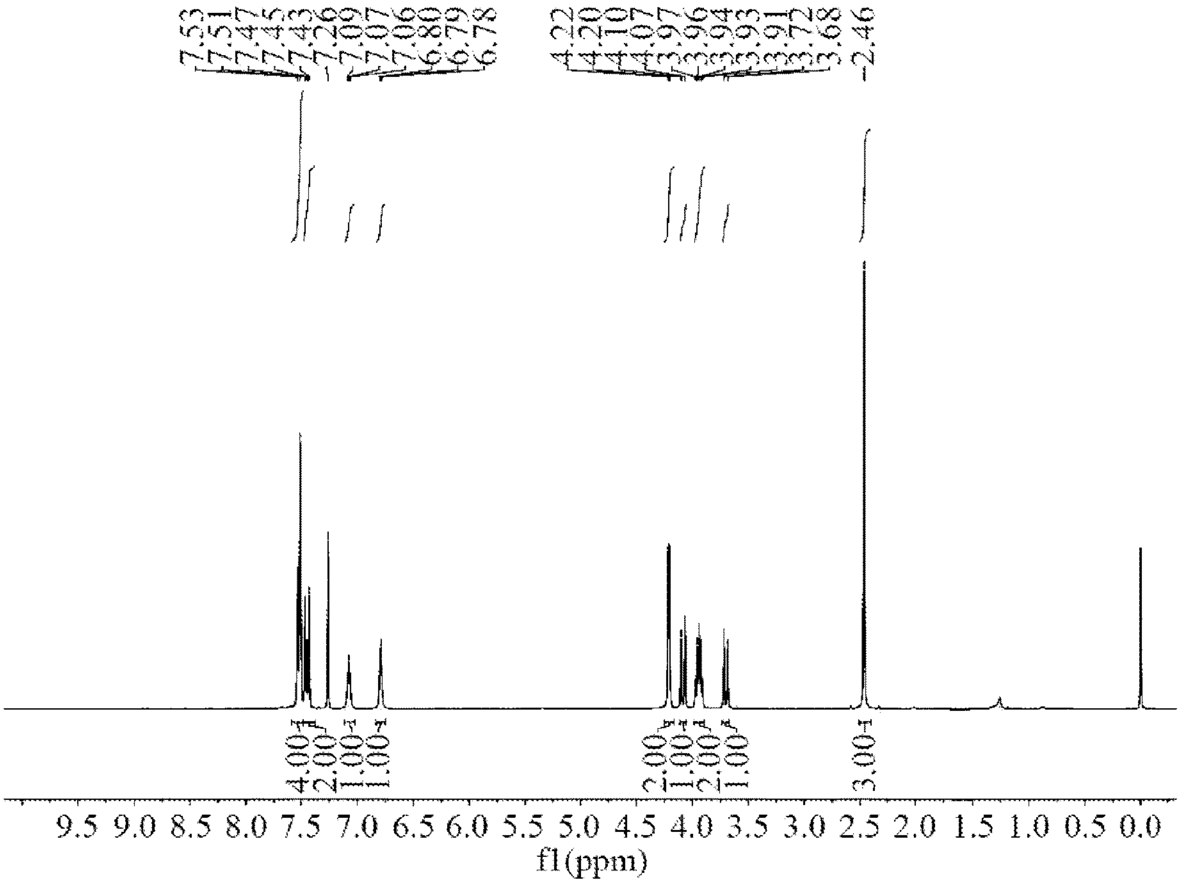
FIG. 2 shows an HNMR spectrum of the fluralaner prepared in Example 1.

FIG. 2 shows an HNMR spectrum of the fluralaner prepared in Example 1. $^1H$ NMR (500 MHz, $CDCl_3$): δ 7.52 (d, J=11.7 Hz, 4H), 7.48-7.38 (m, 2H), 7.07 (t, J=5.9 Hz, 1H), 6.79 (t, J=5.2 Hz, 1H), 4.21 (d, J=5.2 Hz, 2H), 4.08 (d, J=17.2 Hz, 1H), 3.98-3.89 (m, 2H), 3.70 (d, J=17.2 Hz, 1H), 2.46 (s, 3H).

LC detection was conducted on the fluralaner prepared in Example 1 according to the following conditions: instrument: Agilent infinity 1260II; mobile phase (volume ratio): A (0.03% trifluoroacetic acid aqueous solution)/B (acetonitrile) at an initial ratio of 85/15; a gradient elution program was shown in Table 1; flow rate: 0.9 mL/min; running time: 35 min; injection volume: 10 μL; column temperature: 35° C.; wavelength: 256 nm; column: Agilent XDB-C18 4.6×250 mm.

TABLE 1

Gradient elution program for LC detection

| | T (min) | | | | | |
|---|---|---|---|---|---|---|
| | 0 | 10 | 17 | 27 | 27.1 | 35 |
| A | 85% | 35% | 20% | 60% | 85% | 85% |
| B | 15% | 65% | 80% | 40% | 15% | 15% |

Determination method: 25 mg of the finished product was weighed precisely and then added into a 50 mL volumetric flask, and diluted to a constant volume with a diluent (acetonitrile:water at a volume ratio of 60:40).

Figure 3:
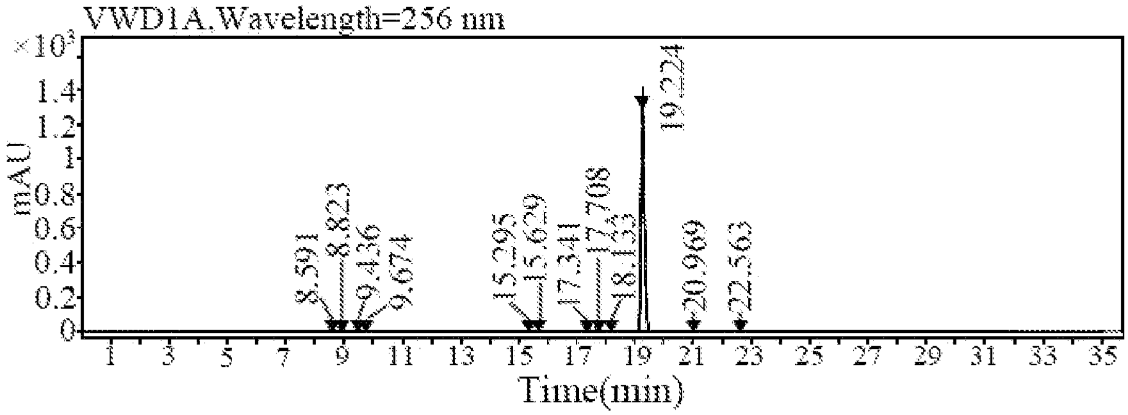
FIG. 3 shows a liquid chromatography (LC) spectrum of the fluralaner prepared in Example 1.

FIG. 3 shows an LC spectrum of the fluralaner prepared in Example 1; from FIG. 3 it can be seen that the fluralaner has a purity of 99.75%.

EXAMPLE 2

418 g of 4-(5-(3,5-dichlorophenyl)-5-(trifluoromethyl)-4,5-dihydro-isoxazol-3-yl)-2-methyl-benzoic acid, 1.0 g of sulfuric acid, 4.0 g of silicotungstic acid, 80 g of ethanol, and 936 g of toluene were added into a reaction vessel equipped with a thermometer, a stirrer, and a water separator. A resulting mixture was subjected to reaction at a temperature of 90° C. to 100° C. for 5 h while fractionating water produced during the reaction, and then cooled to 50° C. to obtain a cooled mixture. 163.5 g of 2-amino-N-(2,2,2-trifluoroethyl)acetamide was added into the cooled mixture and then subjected to reaction at a temperature of 120° C. to 125° C. for 3 h while fractionating ethanol produced during the reaction. After the reaction is completed, filtration was conducted, and a resulting organic layer was washed by using 500 g of hydrochloric acid with a pH of 1 and 300 g of water in sequence. A resulting product was subjected to atmospheric distillation to recover solvent, and a remaining product was dried to obtain 550.1 g of a white solid fluralaner product with a purity of 99.65% and a yield of 98.9%.

EXAMPLE 3

418 g of 4-(5-(3,5-dichlorophenyl)-5-(trifluoromethyl)-4,5-dihydro-isoxazol-3-yl)-2-methyl-benzoic acid, 3.6 g of phosphoric acid, 80 g of an aluminosilicate molecular sieve, 80 g of ethanol, and 3,344 g of toluene were added into a reaction vessel equipped with a thermometer, a stirrer, and a water separator. A resulting mixture was subjected to reaction at a temperature of 90° C. to 100° C. for 5 h while fractionating water produced during the reaction, and then cooled to 50° C. to obtain a cooled mixture. 163.5 g of 2-amino-N-(2,2,2-trifluoroethyl)acetamide was added into the cooled mixture and then subjected to reaction at a temperature of 120° C. to 125° C. for 3 h while fractionating ethanol produced during the reaction. After the reaction is completed, filtration was conducted, and a resulting organic layer was washed by using 500 g of hydrochloric acid with a pH of 1 and 300 g of water in sequence. A resulting product was subjected to atmospheric distillation to recover solvent, and a remaining product was dried to obtain 550.6 g of a white solid fluralaner product with a purity of 99.56% and a yield of 99.0%.

EXAMPLE 4

418 g of 4-(5-(3,5-dichlorophenyl)-5-(trifluoromethyl)-4,5-dihydro-isoxazol-3-yl)-2-methyl-benzoic acid, 1.6 g of p-toluenesulfonic acid, 15 g of sulfonic acid resin, 32 g of methanol, and 1,300 g of toluene were added into a reaction vessel equipped with a thermometer, a stirrer, and a water separator. A resulting mixture was subjected to reaction at a temperature of 70° C. to 80° C. for 10 h while fractionating water produced during the reaction, and then cooled to 50° C. to obtain a cooled mixture. 163.5 g of 2-amino-N-(2,2,2-trifluoroethyl)acetamide was added into the cooled mixture and then subjected to reaction at a temperature of 120° C. to 125° C. for 3 h while fractionating methanol produced during the reaction. After the reaction is completed, filtration was conducted, and a resulting organic layer was washed by using 500 g of hydrochloric acid with a pH of 1 and 300 g of water in sequence. A resulting product was subjected to atmospheric distillation to recover solvent, and a remaining product was dried to obtain 551.3 g of a white solid fluralaner product with a purity of 99.58% and a yield of 99.2%.

EXAMPLE 5

418 g of 4-(5-(3,5-dichlorophenyl)-5-(trifluoromethyl)-4,5-dihydro-isoxazol-3-yl)-2-methyl-benzoic acid, 1.6 g of p-toluenesulfonic acid, 1.0 g of sulfuric acid, 15 g of sulfonic acid resin, 320 g of methanol, and 3,000 g of toluene were added into a reaction vessel equipped with a thermometer, a stirrer, and a water separator. A resulting mixture was subjected to reaction at a temperature of 70° C. to 80° C. for 6 h while fractionating water produced during the reaction, and then cooled to obtain cooled to 50° C. a mixture. 163.5 g of 2-amino-N-(2,2,2-trifluoroethyl)acetamide was added into the cooled mixture and then subjected to reaction at a temperature of 120° C. to 125° C. for 3 h while fractionating methanol produced during the reaction. After the reaction is completed, filtration was conducted, and a resulting organic layer was washed by using 500 g of hydrochloric acid with a pH of 1 and 300 g of water in sequence. A resulting product was subjected to atmospheric distillation to recover solvent, and a remaining product was dried to obtain 550.5 g of a white solid fluralaner product with a purity of 99.63% and a yield of 99.0%.

EXAMPLE 6

418 g of 4-(5-(3,5-dichlorophenyl)-5-(trifluoromethyl)-4,5-dihydro-isoxazol-3-yl)-2-methyl-benzoic acid, 1.6 g of p-toluenesulfonic acid, 1.0 g of phosphoric acid, 30 g of sulfonic acid resin, 60 g of methanol, and 2,000 g of cyclohexane were added into a reaction vessel equipped with a thermometer, a stirrer, and a water separator. A resulting mixture was subjected to reaction at a temperature of 70° C. to 80° C. for 6 h while fractionating water produced during the reaction, and then cooled to 50° C. to obtain a cooled mixture. 163.5 g of 2-amino-N-(2,2,2-trifluoroethyl)acetamide was added into the cooled mixture and then subjected to reaction at a temperature of 90° C. to 95° C. for 3 h while fractionating methanol produced during the reaction. After the reaction is completed, filtration was conducted, and a resulting organic layer was washed by using 500 g of hydrochloric acid with a pH of 1 and 300 g of water in sequence. A resulting product was subjected to atmospheric distillation to recover solvent, and a remaining product was dried to obtain 548.1 g of a white solid fluralaner product with a purity of 99.66% and a yield of 98.6%.

EXAMPLE 7

418 g of 4-(5-(3,5-dichlorophenyl)-5-(trifluoromethyl)-4,5-dihydro-isoxazol-3-yl)-2-methyl-benzoic acid, 1.6 g of p-toluenesulfonic acid, 1.0 g of sulfuric acid, 20 g of phosphotungstic acid, 60 g of methanol, and 1,200 g of ethylbenzene were added into a reaction vessel equipped with a thermometer, a stirrer, and a water separator. A resulting mixture was subjected to reaction at a temperature of 70° C. to 80° C. for 6 h while fractionating water produced during the reaction, and then cooled to 50° C. to obtain a cooled mixture. 163.5 g of 2-amino-N-(2,2,2-trifluoroethyl)acetamide was added into the cooled mixture and then subjected to reaction at a temperature of 140° C. to 150° C. for 3 h while fractionating methanol produced during the reaction. After the reaction is completed, filtration was conducted, and a resulting organic layer was washed by using 500 g of hydrochloric acid with a pH of 1 and 300 g of water in sequence. A resulting product was subjected to atmospheric distillation to recover solvent, and a remaining product was dried to obtain 549.7 g of a white solid fluralaner product with a purity of 99.55% and a yield of 98.9%.

EXAMPLE 8

418 g of 4-(5-(3,5-dichlorophenyl)-5-(trifluoromethyl)-4,5-dihydro-isoxazol-3-yl)-2-methyl-benzoic acid, 1.6 g of p-toluenesulfonic acid, 1.0 g of sulfuric acid, 20 g of phosphotungstic acid, 100 g of isopropanol, and 1,200 g of xylene were added into a reaction vessel equipped with a thermometer, a stirrer, and a water separator. A resulting mixture was subjected to reaction at a temperature of 120° C. to 130° C. for 3 h while fractionating water produced during the reaction, and then cooled to 50° C. to obtain a cooled mixture. 163.5 g of 2-amino-N-(2,2,2-trifluoroethyl) acetamide was added into the cooled mixture and then subjected to reaction at a temperature of 140° C. to 150° C. for 3 h while fractionating isopropanol produced during the reaction. After the reaction is completed, filtration was conducted, and a resulting organic layer was washed by using 500 g of hydrochloric acid with a pH of 1 and 300 g of water in sequence. A resulting product was subjected to atmospheric distillation to recover solvent, and a remaining product was dried to obtain 548.6 g of a white solid fluralaner product with a purity of 99.69% and a yield of 98.7%.

EXAMPLE 9

418 g of 4-(5-(3,5-dichlorophenyl)-5-(trifluoromethyl)-4,5-dihydro-isoxazol-3-yl)-2-methyl-benzoic acid, 0.42 g of p-toluenesulfonic acid, 100 g of methanol, and 1,200 g of toluene were added into a reaction vessel equipped with a thermometer, a stirrer, and a water separator. A resulting mixture was subjected to reaction at a temperature of 80° C. to 90° C. for 10 h while fractionating water produced during the reaction, and then cooled to 50° C. to obtain a cooled mixture. 163.5 g of 2-amino-N-(2,2,2-trifluoroethyl)acetamide was added into the cooled mixture and then subjected to reaction at a temperature of 120° C. to 130° C. for 12 h while fractionating methanol produced during the reaction. After the reaction is completed, filtration was conducted, a resulting organic layer was washed by using 500 g of hydrochloric acid with a pH of 1 and 300 g of water in sequence. A resulting product was subjected to atmospheric distillation to recover solvent, and a remaining product was dried to obtain 547.7 g of a white solid fluralaner product with a purity of 99.66% and a yield of 98.5%.

EXAMPLE 10

418 g of 4-(5-(3,5-dichlorophenyl)-5-(trifluoromethyl)-4,5-dihydro-isoxazol-3-yl)-2-methyl-benzoic acid, 1.6 g of p-toluenesulfonic acid, 1.0 g of sulfuric acid, 20 g of phosphotungstic acid, 120 g of n-propanol, and 1,400 g of ethylbenzene were added into a reaction vessel equipped with a thermometer, a stirrer, and a water separator. A resulting mixture was subjected to reaction at a temperature of 120° C. to 130° C. for 3 h while fractionating water produced during the reaction, and then cooled to 50° C. to obtain a cooled mixture. 163.5 g of 2-amino-N-(2,2,2-trifluoroethyl)acetamide was added into the cooled mixture and then subjected to reaction at a temperature of 135° C. to 145° C. for 3 h while fractionating n-propanol produced during the reaction. After the reaction is completed, filtration was conducted, and then a resulting organic layer was washed by using 500 g of hydrochloric acid with a pH of 1 and 300 g of water in sequence. A resulting product was subjected to atmospheric distillation to recover solvent, and a remaining product was dried to obtain 552.0 g of a white solid fluralaner product with a purity of 99.58% and a yield of 99.3%.

EXAMPLE 11

418 g of 4-(5-(3,5-dichlorophenyl)-5-(trifluoromethyl)-4,5-dihydro-isoxazol-3-yl)-2-methyl-benzoic acid, 1.6 g of p-toluenesulfonic acid, 1.0 g of sulfuric acid, 15 g of sulfonic acid resin, 200 g of methanol, and 2,000 g of toluene were added into a reaction vessel equipped with a thermometer, a stirrer, and a water separator. A resulting mixture was subjected to reaction at a temperature of 70° C. to 80° C. for 6 h while fractionating water produced during the reaction, and then cooled to 50° C. to a cooled obtain mixture. 156 g of 2-amino-N-(2,2,2-trifluoroethyl)acetamide was added into the cooled mixture and then subjected to reaction at a temperature of 120° C. to 125° C. for 3 h while fractionating methanol produced during the reaction. After the reaction is completed, filtration was conducted, and a resulting organic layer was washed by using 500 g of water and 300 g of water in sequence. A resulting product was subjected to atmospheric distillation to recover solvent, and a remaining product was dried to obtain 546.2 g of a white solid fluralaner product with a purity of 99.59% and a yield of 98.2%.

EXAMPLE 12

418 g of 4-(5-(3,5-dichlorophenyl)-5-(trifluoromethyl)-4,5-dihydro-isoxazol-3-yl)-2-methyl-benzoic acid, 1.6 g of p-toluenesulfonic acid, 1.0 g of sulfuric acid, 15 g of sulfonic acid resin, 200 g of methanol, and 2,500 g of toluene were added into a reaction vessel equipped with a thermometer, a stirrer, and a water separator. A resulting mixture was subjected to reaction at a temperature of 70° C. to 80° C. for 6 h while fractionating water produced during the reaction, and then cooled to 50° C. to obtain of a cooled mixture. 468 g 2-amino-N-(2,2,2-trifluoroethyl)acetamide was added into the cooled mixture and then subjected to reaction at a temperature of 120° C. to 125° C. for 3 h while fractionating methanol produced during the reaction. After the reaction is completed, filtration was conducted, and a resulting organic layer was added 500 g of water, adjusted to a pH of 7 with hydrochloric acid, and then separated. An organic layer obtained after the separation was washed with 300 g of water. A resulting product was subjected to atmospheric distillation to recover solvent, and a remaining product was dried to obtain 546.6 g of a white solid fluralaner product with a purity of 99.52% and a yield of 98.3%.

Although the present disclosure is described in detail by the above examples, these examples are only a part of, not all of, the embodiments of the present disclosure. Other embodiments may also be obtained by persons based on the examples without creative efforts, and all of these embodiments shall fall within the scope of the present disclosure.

What is claimed is:

1. A method for preparing fluralaner, comprising the following steps:

mixing 4-(5-(3,5-dichlorophenyl)-5-(trifluoromethyl)-4,5-dihydro-isoxazol-3-yl)-2-methyl-benzoic acid, a catalyst, an alcohol and an organic solvent to obtain a mixture, and subjecting the mixture to esterification to obtain an esterification solution containing 4-(5-(3,5-dichlorophenyl)-5-(trifluoromethyl)-4,5-dihydro-isoxazol-3-yl)-2-methyl-benzoate; and mixing the esterification solution and 2-amino-N-(2,2,2-trifluoroethyl)acetamide to obtain a mixed solution, and subjecting the mixed solution to ester decomposition-amidation to obtain the fluralaner.

2. The method according to claim 1, wherein the catalyst is one or more selected from the group consisting of p-toluenesulfonic acid, sulfuric acid, phosphoric acid, sulfonic acid resin, phosphotungstic acid, silicotungstic acid, and an aluminosilicate molecular sieve.

3. The method according to claim 1, wherein a weight ratio of the catalyst to the 4-(5-(3,5-dichlorophenyl)-5-(trifluoromethyl)-4,5-dihydro-isoxazol-3-yl)-2-methyl-benzoic acid is in a range of (0.001-0.2):1.

4. The method according to claim 1, wherein the alcohol is one or more selected from the group consisting of methanol, ethanol, isopropanol, and n-propanol.

5. The method according to claim 1, wherein a molar ratio of the alcohol to the 4-(5-(3,5-dichlorophenyl)-5-(1-10):1.

6. The method according to claim 1, wherein the organic solvent is one or more selected from the group consisting of toluene, xylene, ethylbenzene, and cyclohexane.

7. The method according to claim 1, wherein a weight ratio of the organic solvent to the 4-(5-(3,5-dichlorophenyl)-5-(trifluoromethyl)-4,5-dihydro-isoxazol-3-yl)-2-methyl-benzoic acid is in a range of (2-8):1.

8. The method according to claim 1, wherein the esterification is conducted at a temperature of 70° C. to 130° C. for 2 h to 10 h.

9. The method according to claim 1, wherein a molar ratio of the 2-amino-N-(2,2,2-trifluoroethyl)acetamide to the 4-(5-(3,5-dichlorophenyl)-5-(trifluoromethyl)-4,5-dihydro-isoxazol-3-yl)-2-methyl-benzoic acid is in a range of (1-3):1.

10. The method according to claim 1, wherein the ester decomposition-amidation is conducted at a temperature of 90° C. to 150° C. for 3 h to 12 h.

11. The method according to claim 2, wherein a weight ratio of the catalyst to the 4-(5-(3,5-dichlorophenyl)-5-(trifluoromethyl)-4,5-dihydro-isoxazol-3-yl)-2-methyl-benzoic acid is in a range of (0.001-0.2):1.

12. The method according to claim 4, wherein a molar ratio of the alcohol to the 4-(5-(3,5-dichlorophenyl)-5-(trifluoromethyl)-4,5-dihydro-isoxazol-3-yl)-2-methyl-benzoic acid is in a range of (1-10):1.

13. The method according to claim 6, wherein a weight ratio of the organic solvent to the 4-(5-(3,5-dichlorophenyl)-5-(trifluoromethyl)-4,5-dihydro-isoxazol-3-yl)-2-methyl-benzoic acid is in a range of (2-8):1.

14. The method according to claim 9, wherein the ester decomposition-amidation is conducted at a temperature of 90° C. to 150° C. for 3 h to 12 h.

* * * * *